United States Patent [19]

Connor et al.

[11] Patent Number: 4,939,133

[45] Date of Patent: Jul. 3, 1990

[54] N-SUBSTITUTED-2-HYDROXY-α-OXO-BENZENEACETAMIDES AND PHARMACEUTICAL COMPOSITIONS HAVING ACTIVITY AS MODULATORS OF THE ARACHIDONIC ACID CASCADE

[75] Inventors: David T. Connor; Daniel L. Flynn; Wiaczeslaw A. Cetenko; Jagadish C. Sircar, all of Ann Arbor, Mich.; Charles F. Schwender, Califon, N.J.; Elizabeth A. Johnson, Corte Madera, Calif.; Roderick J. Sorenson; Paul C. Unangst, both of Ann Arbor, Mich.

[73] Assignee: Warner-Lambert Company, Morris Plains, N.J.

[21] Appl. No.: 782,763

[22] Filed: Oct. 1, 1985

[51] Int. Cl.$^5$ .................. C07C 233/15; C07C 233/29; C07C 233/66; C07C 233/75

[52] U.S. Cl. ........................... 514/166; 514/601; 540/1; 540/362; 548/577; 560/9; 560/10; 560/12; 560/13; 560/21; 560/45; 564/99; 564/161; 564/166; 564/167; 564/169; 564/153; 564/154; 564/155; 564/173; 564/179

[58] Field of Search ............... 564/169, 200, 199, 179, 564/170; 514/166, 616, 617, 621, 625, 622, 617; 562/459

[56] References Cited

U.S. PATENT DOCUMENTS

| | | | |
|---|---|---|---|
| 3,646,199 | 2/1972 | Scheffenbaum et al. | 564/179 |
| 4,158,063 | 6/1979 | Hitzel et al. | 514/622 |
| 4,562,201 | 12/1985 | Stout et al. | 564/170 |
| 4,742,083 | 9/1985 | Ritchey | 514/617 |

FOREIGN PATENT DOCUMENTS

| | | | |
|---|---|---|---|
| 0076721 | 4/1983 | European Pat. Off. | 562/459 |
| 0113751 | 9/1980 | Japan | 514/621 |
| 0623356 | 9/1981 | U.S.S.R. | 514/621 |

OTHER PUBLICATIONS

Chem. Abstracts, vol. 84, No. 22, May 31, 1976, page 93, No. 155204s (c/o Fuji Photo Film, JP-A-75 161525, 12/27/75).

Chem. Abstracts, vol. 76, No. 5, Jan. 31, 1972, page 343, No. 24952g (c/o Nealey et al., J. Chem. Eng. Data 1971, 16(4), pp. 482–483).

Chem. Abstracts, vol. 86, No. 21, May 23, 1977, page 440, No. 155310a (c/o Kenji et al., Nippon Kagaku Kaishi, 1976, (12), 1899-903).

Mashevskaya et al., (Perm. Farm. Inst.), Izv Vyssh. Uchebn. Faved., Khem. Khim. Tekhnol. 1979, 22(11), pp. 1323–1326.

EPO Search Report with attachments.

Primary Examiner—Richard L. Raymond
Assistant Examiner—Kristina Konstas
Attorney, Agent, or Firm—Joan Thierstein

[57] ABSTRACT

The present invention relates to novel N-substituted 2-hydroxybenzamide and N-substituted 2-hydroxy-α-oxo-benezene acetamide compounds pharmaceutical compositions, and methods of use for therefore for the treatment of diseases in which products having lipoxygenase enzyme activity contribute to the pathological condition. Selected novel intermediates are also the present invention.

12 Claims, No Drawings

N-SUBSTITUTED-2-HYDROXY-α-OXO-BENZENEACETAMIDES AND PHARMACEUTICAL COMPOSITIONS HAVING ACTIVITY AS MODULATORS OF THE ARACHIDONIC ACID CASCADE

BACKGROUND OF THE INVENTION

The present invention relates to novel compounds, pharmaceutical compositions, and methods of use for the treatment of diseases in which products of lipoxygenase enzyme activity or the action of leukotrienes contribute to the pathological condition. Selected novel intermediates are also the present invention. The novel 2-hydroxybenzamides and N-substituted-2-hydroxy-α-oxo-benzeneacetamides of the present invention are lipoxygenase inhibitors providing activity useful for treating asthma, allergies, cardiovascular diseases, migraines, and immunoinflammatory conditions.

More particularly, this invention concerns certain novel 2-hydroxybenzamides and novel 2-hydroxy-α-oxo-benzeneacetamides having the Formula I as defined below, pharmaceutical compositions having the novel 2-hydroxybenzamides and novel 2-hydroxy-α-oxobenzeneacetamides therein, and methods of use therefore in the treatment or amelioration of diseases in which products of lipoxygenase enzyme activity or the reaction of leukotrienes contribute to the pathological condition. Lipoxygenase enzymes are part of the arachidonic acid cascade.

Arachidonic acid serves as the biological precursor for a family of physiologically active eicosanoids. These include products derived from the action of cyclooxygenase such as the class of prostaglandin-E and -F compounds, thromboxanes, and prostacyclin, and products derived from the action of lipoxygenase enzymes such as hydroxy- and hydroperoxyeicosatetraenoic acids and the leukotrienes.

Lipoxygenase pathway products such as the leukotrienes B4, C4, D4, and E4, 5-hydroxyeicosatetraenoic acid, 5-hydroperoxyeicosatetraenoic acid, and 12-hydroxyeicosatetraenoic acid are involved in the condition recognized as inflammation, and in allergic and immune responses.

These lipoxygenase products have been shown to be highly potent stereospecific inducers of polymorphonuclear leukocyte migration or chemotaxis, lysosomal enzyme release, and degranulation. Additionally, these products induce the contraction of smooth muscle such as vascular and pulmonary tissue, and induce the generation of additional inflammogens such as thromboxane A2 and prostacyclin. Lipoxygenase products also interact with vasodilator prostanoids and other mediators, leading to the enhancement or amplification of the inflammatory response.

Leukotrienes and the hydroxy- and hydroperoxyeicosatetraenoic acids play a major role in the pathogenesis of many disease conditions. These compounds have been found in synovial fluid of rheumatoid joints, in involved skin of psoriatic patients, in inflammed colonic tissue, and at elevated levels in ischemic myocardial tissue. They are also mediators of allergic and asthmatic conditions.

Compounds and pharmaceutical compositions in accordance with the present invention inhibit lipoxygenase or the biosynthesis or biochemical action of leukotrienes and, therefore, are useful in the treatment or amelioration of a number of diseases whose pathogenesis involves the production of the leukotrienes and other lipoxygenase-derived products. These lipoxygenase inhibitors aid in the prevention of tissue damage and inflammation which result from infiltration of leukocytes, release of tissue-digesting lysosomal enzymes, and changes in the permeability and contractile state of smooth muscle tissue.

Specific conditions in which such lipoxygenase-inhibiting compounds and pharmaceutical compositions in accordance with the present invention are useful include allergy; asthma; arthritis; skin disorders including psoriasis and acne; inflammation; inflammatory bowel diseases; pain; and cardiovascular disorders including myocardial ischemia and infarction, angina, arrhythmias, stroke, and atherosclerosis.

"Derivatives of 3-, 4-, and 5-phenylsalicylamides" by H. Jules, et al, J. Am. Pharm. Assoc., Sci. Ed. 45, 277-81 (1956) as reviewed in CA50:16715 describes selected phenylsalicylamides having a phenyl substituent on the phenyl moiety of the phenylsalicylamides and thus differing from the present invention.

Also falling within the scope of the present invention are the pharmaceutically acceptable acid and base addition salts of the compounds of the present invention.

SUMMARY OF THE INVENTION

The present invention are compounds of the Formula I and pharmaceutically acceptable salts thereof wherein:

(1) y is one or two;

(2) b is zero, one, two, three, or four;

(3) $R_1$ is selected from a group consisting of alkyl of from one to four carbons, inclusive, alkoxy of from one to four carbons, inclusive, thioalkoxy of from one to four carbons, inclusive, carbalkoxy of from two to four carbons, inclusive, alkanoyl of from one to four carbons, hydroxy, halogen, nitro, amino, mono- and dialkylamino having each alkyl the same or different from one to four carbons, inclusive, carboalkoxyamido of from one to four carbons, inclusive, alkylsulfinyl of from one to four carbons, inclusive, alkylsulfonyl of from one to four carbons, inclusive, and where b is one then $R_1$ may also be —(CH=CH—CH=CH)— taken together with adjacent ring carbons to form a benzo radical;

(4) $R_5$ is hydrogen; alkyl of from one to four carbons, inclusive; alkoxy of from one to four carbons, inclusive; carbalkoxy of from two to four carbons, inclusive; hydroxy, halogen, or —(CH=CH—CH=CH)— taken together with adjacent carbons to form a benzo radical;

(5) $R_6$ is (a) alkyl of from six to twenty carbons, (b) —CH=CH—$R_4$, (c) —$(CH_2)_n COR_4$ or (d) —$(CH_2)_n$—$R_4$ wherein n is zero to four, inclusive, and $R_4$ is phenyl optionally substituted at the two through six positions by lower alkoxy carbonyl, carbalkoxy having alkoxy of from one to four carbons, inclusive, alkyl of from one to four carbons, alkoxy or thioalkoxyl of from one to four carbons, inclusive, phenalkoxy, amino, monoalkyl or dialkyl amino having the alkyl of from one to four carbons, inclusive, alkanoylamino of from two to six carbons, inclusive, carboxyl, halogen, hydroxy, hydroxyalkyl of from one to four carbons, inclusive, alkanoyl of from one to four carbons, inclusive, nitro, or alkanesulfonamido of from one to four carbons;

(6) X is hydrogen or lower alkyl of from one to four carbons, inclusive.

One group of preferred compounds of Formula I include compounds wherein $R_1$ is hydrogen, y is 1, $R_5$ is H, and $R_6$ is alkyl of from 6 to 20 carbons, inclusive, or —$(CH_2)_n$ $R_4$ wherein n is two and $R_4$ is phenyl optionally substituted by carboxyl, carboalkyoxy of from one to four carbons, inclusive, chloro, alkoxy of from one to four carbons, inclusive, hydroxy, or phenyl; or the pharmaceutically acceptable acid or base addition salts thereof..

Another group of preferred compounds of Formula I include compounds wherein $R_1$ is hydrogen, y is 2, $R_5$ is hydrogen or the benzo radical; $R_6$ is alkyl of from 6 to 20 carbons, inclusive, or —$(CH_2)_n$—$R_4$ wherein n is 2 and $R_4$ is phenyl optionally substituted by lower alkoxycarbonyl; carboxyl, carboalkoxy wherein the alkoxy is from one to four carbons, inclusive, alkoxy of from one to four carbons, inclusive, hydroxy, or pharmaceutically acceptable acid or base addition salts.

Thus, the more preferred compounds of Formula I are:

N-[4-[2-(3,4-dimethoxyphenyl)ethyl]phenyl]-2-hydroxy-α-oxo-benzeneacetamide.

N-[4-[2-(3,4-dihydroxyphenyl)ethyl]phenyl]-2-hydroxy-α-oxo-benzeneacetamide.

N-[4-[2-(3,4-dihydroxyphenyl)ethyl]phenyl]-2-hydroxy-benzamide.

N-[4-[2-(3,4-dihydroxyphenyl)ethyl]phenyl]-2-hydroxy-4-methylbenzamide.

N-[4-[2-(3,4-dihydroxyphenyl)ethyl]phenyl]-3-(1,1-dimethylethyl)-2-hydroxy-α-oxobenzeneacetamide.

N-[4-[2-(3,4-dihydroxyphenyl)ethyl]phenyl]-2-hydroxy-4-methoxybenzamide.

N-[4-[2-(3,4-dihydroxyphenyl)ethyl]phenyl]-2-hydroxy-N,4-dimethylbenzamide.

The present invention is also a pharmaceutical composition comprising an effective amount of a compound having the Formula I as defined above together with a pharmaceutically acceptable carrier. An effective amount is the amount useful for treating or ameliorating a number of diseases or conditions comprising an inhibition of a lipoxygenase effect. The diseases or conditions are readily recognized for the pathogenesis affected by lipoxygenase effect, and are recited specifically above.

Thus, in accordance with the present invention, another aspect of the invention, provides a method of administering to mammals, including humans, in need of treatment or amelioration of diseases or conditions an amount effective for treatment of the diseases or conditions as denoted above of a compound or composition having the Formula I as defined above.

The antiasthma and antiallergic activity provides methods of treatment for hypersensitivity reaction having broad symptoms. For example, the symptoms may include dermatitis, lacrimation, nasal discharge, coughing, sneezing, nausea, vomiting, diarrhea, difficulty in breathing, pain, inflammation, and in severe cases, anaphylatic shock and circulatory collapse. The symptoms may be found in man as well as other animals suffering from bronchial asthma, seasonal pollinosis (e.g., hayfever), allergic rhinitis, urticaria, allergic conjunctivitis, food allergies, and anaphylactoid reactions.

Likewise, the activity of the compounds of Formula I provides a method of treatment for cardiovascular disorders, particularly ischemia and myocardial infarctions. The symptoms of a subject having a cardiovascular disorder may be determined by special diagnostic procedures directed to subjects having a history, general physical appearance and then detailed deviations from normal appearances suggesting a cardiovascular disorder. Such disorders are also found in man as well as other mammals. Symptoms of the disorders are described extensively in *The Merck Manual* 14th ed, (1982).

Further, method of treatment is provided by the compounds of Formula I herein for migraine and inflammation. The symptoms requiring treatment for these purposes are also readily recognized, particularly for migraine in man and/or inflammation in man as well as other mammals.

Pharmaceutical compositions which also are the present invention are prepared from the compound of Formula I and salts thereof described as the present invention having inert pharmaceutical carriers. The compositions may be either solid or liquid.

A physician or veterinarian of ordinary skill readily determines a subject who is exhibiting symptoms described herein. Regardless of the route of administration selected, the compounds of the present invention are formulated into pharmaceutically acceptable dosage forms by conventional methods known to the pharmaceutical art.

The compounds can be administered in such oral unit dosage forms such as tablets, capsules, pills, powders, or granules. They also may be administered rectally or vaginally in such forms as suppositories or bougies; they may also be introduced parenterally (e.g., subcutaneously, intravenously, or intramuscularly), using forms known to the pharmaceutical art. They are also introduced directly to an affected area (e.g., in the form of eye drops or by inhalation). For the treatment of asthma or allergies such as erythema, and inflammatory skin disorders (psoriasis), the compounds of the present invention may also be administered topically in the form of ointments, creams, gels, or the like.

An effective but nontoxic quantity of the compound is employed in treatment. The ordinarily skilled physician or veterinarian will readily determine and prescribe the effective amount of the compound to prevent or arrest the progress of the condition for which treatment is indicated. In so proceeding, the physician or veterinarian could employ relatively low dosages at first, subsequently increasing the dose until a maximum response is obtained.

Initial dosages of the compounds of the invention having Formula I are ordinarily in the area of 10 mg up to 2 g per day orally, preferably 10 mg to 500 mg per dose orally, given from one to four times daily or as needed. When other forms of administration are employed equivalent doses are administered.

The compounds of the invention are capable of forming both pharmaceutically acceptable acid addition and/or base salts. Base salts are formed with metals or amines, such as ammonium, alkali, and alkaline earth metals or organic amines. Examples of metals used as cations are sodium, potassium, magnesium, calcium, and the like. Examples of suitable amines are N,N'dibenzylethylenediamine, chloroprocaine, choline, diethanolamine, ethylenediamine, N-methylflucamine, and procaine.

Pharmaceutically acceptable acid addition salts are formed with organic and inorganic acids.

Examples of suitable acids for salt formation are hydrochloric, sulfuric, phosphoric, acetic, citric, malonic, salicyclic, malic, gluconic, fumaric, succinic, ascorbic, maleic, methanesulfonic, arginine, and the like. The salts are prepared by contacting the free base form with a sufficient amount of the desired acid to produce either a mono or di, etc salt in the conventional manner. The free base forms may be regenerated by treating the salt form with a base. For example, dilute solutions of aqueous base may be utilized. Dilute aqueous sodium hydroxide, potassium carbonate, ammonia, and sodium bicarbonate solutions are suitable for this purpose. The free base forms differ from their respective salt forms somewhat in certain physical properties such as solubility in polar solvents, but the salts are otherwise equivalent to their respective free base forms for purposes of the invention.

The compounds of the invention can exist in unsolvated as well as solvated forms, including hydrated forms. In general, the solvated forms, including hydrated forms and the like are equivalent to the unsolvated forms for purposes of the invention.

Finally, the methods of preparation and selected novel intermediates for preparation for compounds of Formula I as defined above are also the present invention.

Generally, a method of preparation of the compounds of Formula I as defined above can be accomplished as shown in Scheme I wherein $R_1$, b, Y, X, and $R_5$, and $R_6$ are as defined above and R is hydrogen, lower alkyl, or phenyl.

When R is hydrogen preparation of the compound of Formula I wherein y is one, is shown in Scheme I (A). The preparation may be accomplished by reacting the salicyclic acid of Formula II wherein R is hydrogen with dicyclohexylcarbodiimide or carbonyldiimidazole and the desired compound of Formula III in an inactive solvent, such as tetrahydrofuran, methylene chloride, or ethylene dichloride or mixtures thereof under nitrogen at from about 0° C. to about room temperature for from 50 minutes to 24 hours. Optimum conditions vary within reasonable experimentation depending upon the reactants.

Alternatively, when R is lower alkyl or phenyl the preparation of the compound of Formula I wherein y is one or two shown in Scheme I (A) may be accomplished by reacting the ester of Formula II wherein R is lower alkyl or phenyl in the presence of butyl lithium, diisopropylamine, and the desired aniline of Formula III. An inert organic solvent such as tetrahydrofuran is used in the reaction which is maintained at ice bath temperature with an ice bath for from ten minutes to two hours. See, for example, K. W. Yank, et al, *Tetrahedron Letters*, 1791 (1970).

According to Scheme I (B) a slight excess of the compound of the Formula II$_1$ wherein $R_1$ and b are as defined above, is heated with the compound of Formula III at from 24° to 240° C., preferably of from 140° to 210° C. under argon for about two to five hours.

Additionally, the compound of Formula I can be prepared by the method shown in Scheme I (C) where a slight excess of the compound of Formula II$_2$ is reacted with a compound of Formula III in a nonprotic solvent such as tetrahydrofuran, and the like.

Specific variations within the above general description may include, for example, preparation of compounds of Formula I wherein $R_4$ includes phenyl optionally substituted by at least one hydroxy group by treatment of corresponding methoxy groups with boron tribromide, hydrobromic acid or trimethylsilyliodide using appropriate conditions. Preferred solvents are dichloroethane or dichloromethane. For example, see also M. V. Bhatt and S. U. Kulkarmi, *Synthesis* (4), 249 (1983) for a review of the cleavage of ethers.

The intermediates of Formula III wherein $R_6$ is alkyl of from six to twenty carbons, inclusive, are known or can be readily prepared by an ordinarily skilled artisan. However, the novel intermediate of Formula III wherein $R_6$ is —CH=CH—$R_4$ and —(CH$_2$)$_n$—$R_4$ or (CH$_2$)$_n$COR$_4$ are prepared by a synthetic sequence as shown for III$_2$, III$_3$, and III$_4$ in Schemes III or IV, respectively. More specifically, the compound of Formula IV$_1$, wherein $R_7$ are the optional substituents for the phenyl as defined above for $R_4$, b is an integer of from zero to five, and $R_5$ is as defined above; is prepared in a manner shown in Scheme II which is analogous to the method disclosed by P. Pfeiffer and S. Sergiewskaya, *Ber.*, 44:1109 (1911). Subsequent reduction of compounds of Formula IV$_1$ is accomplished by either H$_2$ and Raney nickel or iron and hydrochloric acid or dithionite to produce the compound of Formula III$_2$ or Formula III$_3$, respectively, wherein $R_7$ and $R_5$ are as defined above. The reduction is carried out in conditions within the ranges known for the reagents. Reduction of IV$_1$ by catalytic hydrogenation using a Raney nickel catalyst within the range of conditions known for this reduction produces compounds of Formula III$_2$ reducing both the nitro-moiety and unsaturation of the hydrocarbon chain in —CH=CH—$R_4$ of the $R_6$ definition with the compound of Formula I above. Reduction of IV$_1$ with iron and HCl or dithionite selectively reduces the nitro moiety.

Intermediate compounds of Formula III$_4$ wherein $R_5$ and $R_7$ are as defined above are obtained by catalytic addition of H$_2$ to the compound of Formula IV$_2$ over a palladium/carbon catalyst using conditions within those known or without unreasonable experimentation for hydrogenation using H$_2$ with these catalysts. Scheme IV shows the hydrogenation of the intermediate precursor having Formula IV$_2$ to obtain III$_4$. The compounds of Formula IV$_2$ having $R_5$ and $R_7$ as defined above are prepared in a manner analogous to known Freidel-Crafts acylation methods as disclosed by Tadkod, et al, *J. Karntack Univ.*, 3:78–80 (1958).

The intermediates of Formula II wherein $R_1$, b, and R are as defined above and y is one are known or are synthesized by a process analogous to those known in the art. The intermediates of Formula II wherein $R_1$, b, and R are as defined above and y is two, generally, are prepared by reacting a salicyladehyde type compound of Formula XXII with trimethylsilyl cyanide in the presence of a trace amount of zinc iodide at a temperature of about 0° C. to +25° C., preferably 0° to 10° C. for about four to twelve hours in an inert atmosphere. The treatment of salicyladehyde is analogous to the Showalter and Haskell, *J. Heterocyclic Chem.*, 18, 367 (1981), disclosure. The resulting α,2-bistrimethylsiloxybenzeneacetonitrile having an (R$_1$)$_b$ substituent defined above and as shown by Formula XII is added at the rate of one equivalent over a 20 to 30 minute period to hexamethyldisilazane which is previously treated at about 0° C. under an inert atmosphere with from one to slightly more than one equivalent of n-butyllithium and after the treated hexamethyldisilazane is stirred at about 10° C. for from 10 to 30 minutes and then cooled to at least about −78° C. The mixture of α,2-bistrimethylsiloxybenzeneacetonitrile with treated and stirred hexamethyldisilazane is stirred for an additional hour. Lower alkyl, preferably methyl or ethyl chloroformate is added to the mixture, stirred, and then warmed. See Scheme V.

Compounds of Formula I wherein X is lower alkyl may be prepared by a process step analogous to known methods.

Under certain circumstances it is necessary to protect either the N or O of intermediates in the above noted process with suitable protecting groups which are known. Introduction and removal of such suitable oxygen and nitrogen protecting groups are well known in the art of organic chemistry; see for example "Protective Groups in Organic Chemistry," J. F. W. McOmie, ed., (New York, 1973), pages 43ff, 95ff; J. F. W. McOmie, *Advances in Organic Chemistry*, Vol. 3, 191–281 (1963); R. A. Borssonas, *Advances in Organic Chemistry*, Vol. 3, 159–190 (1963); and J. F. W. McOmie, *Chem. & Ind.*, 603 (1979).

Examples of suitable oxygen protecting groups are benzyl, t-butyldimethylsilyl, ethoxyethyl, and the like. Protection of an N—H containing moiety is necessary for some of the processes described herein for the preparation of compounds of this invention. Suitable nitrogen protecting groups are benzyl, triphenylmethyl, trialkylsilyl, trichloroethylcarbamate, trichloroethoxycarbonyl, vinyloxycarbamate, and the like.

Under certain circumstances it is necessary to protect two different oxygens with dissimilar protecting groups such that one can be selectively removed while leaving the other in place. The benzyl and t-butyldimethylsilyl groups are used in this way; either is removable in the presence of the other, benzyl being removed by catalytic hydrogenolysis, and t-butyldimethylsilyl being removed by reaction with, for example, tetra-n-butylammonium fluoride.

In the process described herein for the preparation of compounds of this invention the requirements for protective groups are generally well recognized by one skilled in the art of organic chemistry, and accordingly the use of appropriate protecting groups is necessarily implied by the processes of the charts herein, although not expressly illustrated.

The products of the reactions described herein are isolated by conventional means such as extraction, distillation, chromatography, and the like.

The salts of compounds of Formula I described above are prepared by reacting the appropriate base or acid with a stoichometric equivalent of the acid phenol or N base compounds of Formula I, respectively, to obtain pharmaceutically acceptable salts thereof.

DETAILED DESCRIPTION OF THE INVENTION

By the term, "alkyl of from 6 to 20 carbons, inclusive" is meant any branched or unbranched saturated hydrocarbon grouping having the noted number of carbons, such as hexyl, heptyl, octyl, nonyl, decyl, dodecyl, and the like, and isomers thereof.

The term "alkoxy of from one to four carbons, inclusive" means methoxy, ethoxy, propoxy, or butoxy, and isomers thereof attached to the parent molecular residue through an oxygen atom. Thioalkoxy of from one to four carbons, inclusive, is the same except attached through a sulfur atom.

The term "monoalkyl- or dialkyl-amino having of from one to four carbons, inclusive," means respectively, one or two alkyl groups, as previously defined for of from one to four carbons, inclusive, attached to the parent molecular residue through a nitrogen atom.

The term "alkanoyl of from one to four carbons, inclusive," means a branched or unbranched alkyl, as previously defined for of from one to four carbons, inclusive, attached to the parent molecule residue through the carbonyl group.

The term "hydroxyalkyl of from one to four carbons, inclusive," is an hydroxy attached through an alkyl group, as previously defined for of from one to four carbons, to the parent molecular residue.

The term "alkanoylamino of from two to six carbons, inclusive," means an alkanoyl, as previously defined by including also pentyl or hexyl and isomers thereof among the alkyl attached to the parent molecule residue through the amino group.

The term "carboxyalkoxy having alkoxy of from one to four carbons, inclusive," means an alkyl, as previously defined for alkyl of from one to four carbons, inclusive, attached to the oxygen atom of an ester group, through which the alkyl is attached to the parent molecular residue.

"Halogen" means fluorine, chlorine, bromine, iodine, or trifluoromethyl.

"Carboalkoxyamide of from one to four carbons, inclusive," means an alkyl, as defined above for of from one to four carbons, inclusive, attached to the oxygen atom of an urethane group which is in turn attached to the parent molecule residue through an amino group.

"Alkyl sulfinyl" and "alkyl sulfonyl" are respectively, an alkyl attached to the parent residue molecule through a sulfinyl and sulfonyl group.

DESCRIPTION OF THE PREFERRED EMBODIMENTS

The invention is further elaborated by the representative examples as follows. Such examples are not meant to be limiting thereto.

I. PREPARATION OF COMPOUNDS OF FORMULA IV

A. For compounds of Formula IV, see Scheme II.

PREPARATION A 1,2-Dimethoxy-4-[2-(4-nitrophenyl)ethenyl]benzene (See Scheme II, Formula IV$_1$, R$_7$ is 1,2-dimethoxy, R$_5$ is hydrogen)

A mixture of 272 g (1.5 mole) of p-nitrophenylacetic acid and 249 g (1.5 mole) of 3,4-dimethoxybenzaldehyde in a 2.0 l nitrogen-filled flask is heated to 60° C. (temperature of reaction mixture) on the steam bath. Piperidine (150 ml; 129 g, 1.52 mole) is added to the warm reaction mixture in small portions over 15 minutes. After ~50 ml of piperidine is added, a mild exotherm developed, and the temperature of the reaction mixture rose to 95° C. without external heating. The steam bath is replaced by a heating mantle, and the mixture is heated to reflux over 15 minutes, then maintained at 110°–120° C. for four hours. The reaction mixture is cooled to 70° C. and stirred vigorously while 500 ml of methanol is added. After cooling the mixture in ice, the precipitate that formed is filtered, stirred in 1.0 l of fresh methanol, and refiltered. There is obtained 219 g (51% yield) of olefin product, mp 132°–134° C.

PREPARATION B 1,2-Dichloro-4-[2-(4-nitrophenyl)ethenyl]benzene (See Scheme II, Formula IV, wherein $R_7$ is 1,2-dichloro, and $R_5$ is hydrogen)

Prepared by the procedure described in Preparation A, from p-nitrophenylacetic acid (125 g, 0.69 mole) and 3,4-dichlorobenzaldehyde (121 g, 0.69 mole). There was obtained 70 g (35% yield) of the product, mp 197°–199° C.

In an manner analogous to that found in above preparation using appropriate starting materials, the following compounds are prepared (see Scheme II).

PREPARATION C

4-[2-[(4-Nitrophenyl)ethenyl][1,1-biphenyl] mp 238°–239° C.

PREPARATION D

1-Methoxy-4-[2-(4-nitrophenyl)ethenyl]-2-(phenylmethoxy)benzene, mp 139°–144° C.

PREPARATION E 1,2-Dimethyl-4-[2-(4-nitrophenyl)ethenyl]benzene, mp 113°–115° C.

PREPARATION F 1,3-Dimethoxy-5-[2-(4-nitrophenyl)ethenyl]benzene, mp 145°–146° C.

PREPARATION G

2-[2-(4-Nitrophenyl)ethenyl]naphthalene, mp 168°–170° C.

PREPARATION H 1,2,3-Trimethoxy-5-[2-(4-nitrophenyl)ethenyl]benzene, mp 192°–195° C.

PREPARATION I 1,2-Dimethoxy-3-[2-(4-nitrophenyl)ethenyl]benzene, mp 143°–145° C.

PREPARATION J 2,4-Dimethoxy-1-[2-(4-nitrophenyl)ethenyl]benzene, mp 107°–110° C.

PREPARATION K 1,2-Dimethoxy-4-[2-(2-nitrophenyl)ethenyl]benzene, mp 134°–137° C.

PREPARATION L 1,2-Dibenzyloxy-4-[2-(4-nitrophenyl)ethenyl]benzene p-Nitrophenyl acetic acid (29.2 g, 161 mmole) and 3,4-dibenzyloxybenzaldehyde (51.9 g, 163 mmole) are mixed with piperdine (16 ml), and heated for three hours under a dean stark trap. The product is recrystallized from methanol to afford 36.0 g (51%) of 1,2-dibenzyloxy-4-[nitrophenyl)ethenyl]benzene, mp 138°–141° C.

B. For compounds of Formula $IV_2$ see Scheme IV.

PREPARATION M

N-[2-Methoxy-5-[(4-nitrophenyl)acetyl]phenyl]acetamide (See Scheme IV, Formula $IV_2$ Wherein $R_7$ is 2-methoxy and Acetamide, n is one, and $R_5$ is hydrogen)

A mixture of anhydrous $AlCl_3$ (36 g, 270 mmol) and 50 ml of $CH_2Cl_2$ is cooled to 0° in an ice bath. 2-Acetylanisidine (33 g, 200 mmol) is added to the stirring mixture. A solution of 39.9 g (200 mmol) of 4-nitrophenylacetyl chloride in 130 ml of $CH_2Cl_2$ is added slowly to the cooled reaction mixture. The reaction mixture is stirred at 0° C. for 0.75 hour and 22 hours at room temperature. The reaction mixture is poured onto a mixture of 800 ml ice and 40 ml concentrated hydrochloric acid and allowed to stir for 1.25 hours before extraction with $CH_2Cl_2$. The $CH_2Cl_2$ extract is evaporated to a dark oily residue which crystallized from MeOH to give 28 g (52%) of a yellow solid. Further recrystallization from MeOH gave the pure product, mp 200°–203° C.

In a manner analogous to that found above in Preparation M using appropriate starting materials the following compounds of Formula $IV_2$ are prepared.

PREPARATION N 1-(3,4-Dimethoxyphenyl)-3-(4-nitrophenyl)propanone, mp-126°–132° C.

PREPARATION O 1-(3,4-Dimethoxyphenyl)-4-(4-nitrophenyl)butanone, mp 109°–112° C.

II. Preparation of Compounds of Formula III

A. For compounds of Formula $III_2$ and $III_3$ see Scheme III.

PREPARATION 1

4-[2-(3,4-Dimethoxyphenyl)ethyl]benzeneamine (See Scheme III Formula $III_2$ Wherein $R_7$ is 3,4-dimethoxy, and $R_5$ is Hydrogen A mixture of 19.4 g (0.068 mole) of 1,2-dimethoxy-4-[2-(4-nitrophenyl)ethenyl]benzene as prepared in Preparation A above, and 0.20 g 10% Pd/C catalyst in 200 ml of N,N-dimethylformamide is hydrogenated at 55 psig $H_2$ pressure for 16 hours. The catalyst is removed by filtration, and the filtrate is evaporated. Recrystallization of the residue from methanol yeilded 12.3 g (70% yield) of the amine product, mp 116°–117° C.

PREPARATION 2

4-[2-(3,4-Dichlorophenyl)ethyl]benzenamine (See Scheme III, Formula $III_2$ Wherein $R_7$ is 3,4-dichloro, b is two, and $R_5$ is Hydrogen)

A mixture of 62.3 g (0.21 mole) of 1,2-dichloro-4-[2-(4-nitrophenyl)ethenyl]benzene as prepared in Preparation B above, and 2.0 g of Raney Nickel catalyst in 935 ml of tetrahydrofuran is hydrogenated at 65 psig $H_2$ pressure for 20 hours. The catalyst is removed by filtration, and the filtrate is evaporated. Recrystallization of the residue from hexane/dichloromethane yields 49 g (87% yield) of the amine product, mp 73°–75° C.

In a manner analogous to that found above in Preparations 1 and 2 using appropriate starting materials. The following compounds of Formula $III_2$ are prepared.

PREPARATION 3

4-[2-(1,1'-Biphenyl)-4-ylethyl]benzenamine, mp 109°–111° C.

PREPARATION 4

4-[2-(2-Naphthylenyl)ethyl]benzeneamine, mp 123°–125° C.

PREPARATION 5

4-[2-(3-Hydroxy-4-methoxyphenyl)ethyl]benzenamine, mp 152°–154° C.

PREPARATION 6

4-[2-(3-Methoxyphenyl)ethyl]benzenamine, mp 49°–51° C.

PREPARATION 7

4-[2-(2,3-Dimethoxyphenyl)ethyl]benzenamine·HCl, mp 135°–136° C.

The starting material, 1,2-dimethoxy-3-[2-(4-nitrophenyl)ethenyl]benzene, is as prepared in Preparation I above.

PREPARATION 8

4-[2-(2,4-Dimethoxyphenyl)ethyl]benzenamine, mp 56°–58° C.

The starting material, 2,4-dimethoxy-1-[2-(4-nitrophenyl)ethenyl]benzene, is as prepared in Preparation J above.

PREPARATION 9

4-[2-(3,4,5-Trimethoxyphenyl)ethyl]benzenamine, mp 91°–93° C.

The starting material, 1,2,3-trimethoxy-5-[2-(4-nitrophenyl)ethenyl]benzene, is as prepared in Preparation H above.

PREPARATION 10

4-[2-(3,5-Dimethoxyphenyl)ethyl]benzenamine·HCl, mp 155°–157° C.

The starting material, 1,3-dimethoxy-4-[2-(4-nitrophenyl)ethenyl]benzene, is prepared in a manner analogous to Preparations A through K.

PREPARATION 11

4-[2-(2-Chlorophenyl)ethyl]benzenamine·HCl, mp 208°–211° C.

The starting material, 2-chloro-1-[2-(4-nitrophenyl)ethenyl]benzene, is prepared in a manner analogous to Preparations A through K.

PREPARATION 12

4-[2-(2-Methylphenyl)ethyl]benzenamine·HCl, mp 171°–173° C.

The starting material, 2-methyl-1-[2-(4-nitrophenyl)ethenyl]benezene, is prepared in a manner analogous to Preparations A through K.

PREPARATION 13

4-[2-(4-Butoxyphenyl)ethyl]benzenamine, mp 58°–59° C.

The starting material, 4-butoxy-1-[2-(4-nitrophenyl)ethenyl]benzene, is prepared in a manner analogous to Preparations A through K.

PREPARATION 14

2-[2-(3,4-Dimethoxyphenyl)ethyl]benzenamine, mp 58°–60° C.

The starting material, 1,2-dimethoxy-4-[2-(2-nitrophenyl)ethenyl]benzene, is as prepared in Preparation K above.

PREPARATION 15

N-[2-methoxy-5-[(4-aminophenyl)ethyl]phenyl]acetamide, mp 135°–140° C.

The starting material, N-[2-methoxy-5-[(4-nitrophenyl)ethenyl]phenyl]acetamide, is prepared in a manner analogous to the methods of Preparations A through K.

PREPARATION 16

4-[3-(3,4-dimethoxyphenyl)propyl]benzeamine, mp 54°–57° C.

The starting material, 1,2-dimethoxy-4-[3-(4-nitrophenyl)prop-2-enyl]benzene, is prepared in a manner analogous to Preparations A through K above.

PREPARATION 17

4-[4-(3,4-Dimethoxyphenyl)butyl]benzamine, mp 97°–100° C.

The starting material, 1,2-dimethyl-4-[4-(4-nitrophenyl)but-3-enyl]benzene is prepared in a manner analogous to Preparations A through K above.

B. An alternate method of preparation for a compound of Formula III wherein $R_6$ is $(CH_2)_n$-$R_4$ wherein n is one or two is as follows.

PREPARATION 18

4-[(3,4-Dimethoxyphenyl)methyl]aniline

Mixture of glacial acetic acid (100 ml), 20% Pd/C catalyst (0.5 g) and 3,4-dimethoxy-4'-nitrobenzophenone (Tadkod, Kulkarni, and Nargund, J. Karnatak Univ., 3, 78–80 (1958)) (5.4 g, 18.8 mmol) is hydrogenated at 52 psi for about five hours.

Concentrated $H_2SO_4$ (1.1 ml) and additional 20% Pd/C (0.5 g) are added and the hydrogenation is continued until five equivalents are consumed (21.2 hours). Potassium acetate (2 g, 20 mmol) is added to the mixture and the catalyst is removed by filtration through celite. The filtrate is acidified with concentrated HCl (1.7 ml), concentrated in vacuo to a residual oil and dissolved in 10% HCl (400 ml). The acidic solution is washed with $Et_2O$ (2×400 ml) and $CH_2Cl_2$ (1×100 ml) and then basified with $Na_2CO_3$. The aqueous fraction was extracted with $CH_2Cl_2$ and the $CH_2Cl_2$ extract was dried with $Na_2SO_4$. Evaporation of the volatile solvent in vacuo gave 4.4 g (96%) of crude oily product which crystallized upon standing. The analytical amine was obtained by column chromatography; yield, 1.58 g (35%), mp 101–104.

C. For a salt of a compound of Formula III.

PREPARATION 19

4-[2-(3,4-Dihydroxyphenyl)ethyl]benzenamine as an acetate salt, mp 216°–218° C.

A mixture of 20 g (78 mmol) of 4-[2-[3,4-dimethoxyphenyl)ethyl]aniline which is prepared in Preparation 1 above and 300 ml of 48% hydrobromic acid is stirred at reflux under nitrogen for seven hours and at room temperature overnight. The resultant precipitate is collected, washed with ether, and redissolved in 1 N·NaOH. The solution is acidified to pH 6 with glacial HOAc and the resultant precipitate is collected as crude product. Recrystallization from H₂O and then from MeOH yields the 4-[2-(3,4-dihydroxyphenyl)ethyl]benzenamine as an acetate salt; yield, 13.4 g (76%), mp 216°–218° C.

D. For protected substituents on compounds of Formula III.

PREPARATION 20

4-(3,4-Trimethylsilyloxyphenethyl)aniline

A mixture of 4-(3,4-dihydroxyphenethyl)aniline (34.39 g, 0.15 mole) and hexamethyldisilazane (24.2 g, 0.15 mole) is heated in a wax bath at 120°–160° C. for 3.75 hours under nitrogen, to give dark colored oily residue, which is chromatographed on silica gel (160 g). Elution with chloroform gives oily product (47.1 g, 84%) of satisfactory purity for the next step.

PREPARATION 21

4-[2-(3,4-dibenzyloxyphenyl)ethyl]benzeneamine

The 1,2-dibenzyloxy-4-[2-(4-nitrophenyl)ethenyl]-benzene (10 g, 22 mmole) is dissolved in methanol (50 ml), THF (100 ml) and reacted with Ra—N₁ (1.5 g). Reduction under a pressure of 512 psi at 19.5° C. affords 5.9 g (60%) of 4-[-2-(-3,4-dibenzyloxyphenyl)ethyl]benzenamine, mp 97°–101° C.

PREPARATION 22

N-formyl-4-[2-(3,4-dibenzyloxyphenyl)ethyl]benzenamine

The 4-[2-(3,4-dibenzyloxyphenyl)ethyl]benzenamine (4.5 g, 11 mmole) is dissolved in toluene (75 ml) containing formic acid (0.51 g, 11 mmole) and refluxed for two hours. The reaction mixture is evaporated to dryness, and the residue is recrystallized from toluene to afford 4.7 g (97%) of N-formyl-4-[2-(3,4-dibenyloxyphenyl)ethyl]benzeneamine, mp 119°–122° C.

PREPARATION 23

N-Methyl-4-[2-(3,4-dibenzyloxyphenyl)ethyl]benzenamine

LAH (0.25 g, 6.5 mmole) is added to dry THF (20 ml) under an inert atmosphere, then cooled to ~4° C. (ice/water bath). N-formyl-4-[2-(3,4-dibenzyloxyphenyl)ethyl]benzeneamine (2.9 g, 6.5 mmole) is dissolved in dry THF (20 ml) and added via cannula dropwise to the LAH/THF suspension. The reaction is stirred for 20 hours at ambient temperature under an inert atmosphere. Water (0.25 ml) followed by 15% NaOH (0.25 ml) and finally water (0.75 ml) is added to the reaction mixture. The mixture is filtered, diluted with 0.5 volume of ether, and the organics are washed with brine and then dried (Na₂SO₄). Concentration affords 1.9 g (70% g) of N-methyl-4-[2-(3,4-dibenzyloxyphenyl)ethyl]benzenamine, mp 61°–65° C., of sufficient purity for further use.

PREPARATION 24

N-formyl-4-[2-(3,4-dimethoxyphenyl)ethyl]benzenamine

The 4-[2-(3,4-dimethoxyphenyl)ethyl]benzenamine (9.9 g, 38.9 mmole) is dissolved in toluene (125 ml) containing formic acid (5.0 g, 108 mole) and refluxed for one hour. The reaction mixture is cooled to room temperature and evaporated to dryness. Recrystallization of the residue from toluene affords 11.0 g (82%) of N-formyl-4-[2-(3,4-dimethoxyphenyl)ethyl]benzenamine, mp 128°–130° C.

PREPARATION 25

N-methyl-4-[2-(3,4-dimethoxyphenyl)ethyl]benzeneamine

LAH (1.2 g, 31.6 mole) is added to dry THF (35 ml) under an inert atmosphere then cooled to about 4° C. (ice/water bath). N-formyl-4-[2-(3,4-dimethoxyphenyl)ethyl]benenamine (9.0 g, 31.5 mole) is dissolved in dry THF (35 ml) and added dropwise via a cannula to the LAH/THF suspension. The reaction is stirred for 20 hours at ambient temperature. Water (1.2 ml) is added followed by 15% NaOH (1.2 ml) and finally water (3.6 ml). The mixture is filtered and the filtrate is diluted with 0.5 volume of ether, washed with brine, dried (Na₂SO₄), and concentrated to afford 6.8 g (79%) of N-methyl-4-[2-(3,4-dimethoxyphenyl)ethyl]benzenamine, mp 82°–84° C.

III. Preparation of Compounds of Formula II

PREPARATION I 2,2,7-Trimethyl-4H-1,3,2-benzodioxasilin-4-one. See Scheme I (B) Compound of Formula II₁, Wherein R₁ is methyl A solution of 4-methylsalicylic acid (5.0 g, 33 mmoles) in CHCl₃ (30 mls) is stirred under argon. Pyridine (8.0 mls, 99 mmoles) is added followed by dichlorodimethylsilane (4.0 mls, 33 mmoles) and the mixture is heated to reflux. After 2.5 hours additional pyridine (1 ml, 12 mmoles) and dichlorodimethylsilane (0.5 mls, 4 mmoles) is added and reflux continued for another 30 minutes. The mixture is then cooled and the solvent removed under reduced pressure. The residue is treated with pet ether, filtered off, and rinsed five times with pet ether. The filtrate is evaporated to leave the product, (4.2 g) mp 69°–72° C., suitably pure for subsequent reactions.

PREPARATION II

Step I

5-Chloro-α,2-[(trimethylsilyl)oxy]-benzeneacetonitrile (Formula XII, Scheme 5

A mixture of 5-chlorosalicylaldehyde (12.15 g, 77.6 mmol), trimethylsilylcyanide (16.94 g, 170.7 mmol), and zinc iodide (2 mg) is stirred at 0° C. for four hours under argon atmosphere. The mixture is then allowed to warm to ambient temperature overnight (12 hours). The viscous oil is vacuum-distilled to afford 5-chloro-α2[(trimethylsilyl)oxy]-benzeneacetonitrile, bp 120°–122° C./0.27 mmHg, in 56% yield.

Step II

Ethyl 5-chloro-2-hydroxy-2-oxobenzeneacetate

Hexamethyldisilazane (3.11 g, 19.27 mmol) is dissolved in tetrahydrofuran (20 ml) and cooled to 0° C. under an argon atmosphere. n-Butyllithium (2.3 M, 8.4 ml, 19.27 mmol) is added, and the solution is stirred at 10° C. for 20 minutes followed by cooling to −78° C. At this time, 5-chloro-α,2-[(trimethylsilyl)oxy]-benzenacetonitrile (6.00 g, 18.35 mmol) as prepared in Step I above is added over a 30 minute period. After stirring for an additional hour, ethyl chloroformate (1.95 ml, 20.19 mmol) is added dropwise. The solution is stirred for one hour and then allowed to rise to 10° C. over a 90 minute period. The reaction is quenched by pouring the contents into saturated ammonium chloride solution followed by extraction into dichoromethane. The organics are washed (saturated ammonium chloride solution followed by brine), dried (sodium sulfate), and concentrated to afford a residue. The residue is dissolved in tetrahydrofuran (60 ml). Triethylamine hydrofluoride (5.93 g, 48.99 mmol) is added, and the solution is stirred at 0° C. for 90 minutes. The solution is then concentrated and redissolved in dichloromethane. The organics are washed (1% hydrochloric acid followed by brine), dried (sodium sulfate), and concentrated to give 3.62 g of an oil. Chromatography (Kieselgel 60, dichloromethane) affords ethyl 5-chloro-2-hydroxy-α-oxobenzeneacetate (0.82 g) as a light yellow oil.

PREPARATION III

Following the procedure of Preparation II, Step I, α,2-[(trimethylsilyl)oxy]benzeneacetonitrile is prepared (bp 103°-104° C./1.8 mmHg, 86% yield).

PREPARATION IV

Following the procedure of Preparation II, Step II, ethyl 2-hydroxy-α-oxo-benzeneacetate is prepared (70%).

PREPARATION V 7-(1,1-dimethylethyl)-2,3-benzofurandione (Zwanenburg, Synthesis, 624 (1976)) (See Scheme IC, Compound II$_2$)

A mixture of 2-tert-butylphenol (15 g, 0.1 mmol) and 4-dimethylaminopyridine (0.5 g) is stirred under nitrogen in 300 ml of dichloromethane. Oxalyl chloride (20 ml, 0.22 moles) is added dropwise, then the mixture is heated to reflux. After ten hours the mixture is cooled and the solvent is removed under reduced pressure. The residue is taken up in 100 ml of 1,2-dichloroethane and added dropwise under nitrogen to a suspension of aluminum chloride (40 g, 0.3 mmol) in 300 ml of 1,2-chloroethane. After 20 hours at room temperature the mixture is slowly diluted with water until all solids dissolve. The organic layer is separated and dried over molecular sieves, and the solvent is evaporated to leave a syrup which is taken up in chloroform and filtered through a short column of silica gel. The filtrate is stripped of solvent under reduced pressure to leave the product (9.8 g) as a syrup suitably pure for subsequent reactions.

IV. Preparation of Compounds of Formula I Wherein y is one

EXAMPLE 1

Benzamide, N-[4-[2-(3,4-dimethoxyphenyl)ethyl]phenyl]-2-hydroxy-4-methoxy

A mixture of 4-methoxysalicylic acid (1.00 g, 5.95 mmol), 4-[2-(3,4-dimethoxyphenyl)ethyl]benzenamine (1.53 g, 5.95 mmoll), and dicyclohexylcarbodiimide (1.23 g, 5.95 mmol) in dichloromethane (50 ml) is stirred for 12 hours at ambient temperature. The insoluble dicyclohexylurea is removed by filtration, and the filtrate is concentrated to afford 2.63 g of solid residue. Chromatography (Merck Kieselgel 60, chloroform:ethyl acetate 19:1) of the residue gives N-[4-[2-[(3,4-dimethoxyphenyl)ethyl]phenyl]-2-hydroxy-4-methoxybenzamide (0.89 g, 40%); mp 146°-148° C. after recrystallization from 2-propanol.

Examples 2-7 are prepared by the method of Example 1 and are summarized in Table 1.

TABLE 1

Compounds of Formula I wherein y is one, R$_5$ is hydrogen, b is one, and R$_1$ and R$_6$ are as shown.

| Example | R$_1$ position 3 | 4 | 5 | 6 | R$_6$ | Yield | mp (°C.) |
|---|---|---|---|---|---|---|---|
| 2 | H | OCH$_3$ | H | H | 4-[n-decyl] | 47% | 116-117 |
| 3 | H | OCH$_3$ | H | H | 4-[2-(3,4-bis-trimethyl-siloxyphenyl)-ethyl] | 21% | |
| 4 | H | Ph* | H | H | 4-[2-(3,4-dimethoxy-phenyl)ethyl] | 20% | 190-192 |
| 5 | H | CH$_3$ | H | H | 4-[n-decyl] | 27% | 141-142 |
| 6 | H | Ph | H | H | 4-[n-decyl] | 25% | 154-156 |
| 7 | H | Cl | H | H | 4-[n-decyl] | 13% | 159-160 |

*Ph is phenyl

EXAMPLE 8

N-[4-[2-(3,4-Dihydroxyphenyl)ethyl]phenyl]-2-hydroxy-4-methoxybenzamide

To a solution of N-[4-[2-(3,4-bistrimethylsiloxyphenyl)ethyl]phenyl]-2-hydroxy-4-methoxybenzamide (0.65 g, 1.24 mmol) in methanol (30 ml) is added seven drops of concentrated hydrochloric acid. The solution is then heated to 40°-50° C. for ten minutes. Removal of volatiles gives 0.491 g of a white solid. Recrystallization (2-propanol) affords N-[4-[2-(3,4-dihydroxyphenyl)ethyl]phenyl]-2-hydroxy-4-methoxy benzamide (0.42 g, 90%), mp 179°-180° C., 195°-196° C. (double mp).

EXAMPLE 9

[1,1'-Biphenyl]-3-carboxamide, N-(4-decylphenyl)-2-hydroxy

To a tetrahydrofuran (20 ml) solution of 4-decylaniline (3.07 g, 13.14 mmol), cooled to 0°-5° C. (inert atmosphere), is added n-butyllithium (2.3 M, 13.14 mmol). The deeply colored solution is stirred for ten minutes, after which a tetrahydrofuran (20 ml) solution of methyl 3-phenylsalicylate (1.00 g, 4.38 mmol) is added. The temperature is allowed to rise to 25° C. over a 30 minute period. The reaction is quenched by pouring the contents into 10% hydrochloric acid (100 ml). The organics are extracted into ethyl acetate, washed with 10% hydrochloric acid, dried (sodium sulfate), and concentrated to give 2.77 g of crude solid. Chromatography (Kieselgel 60, dichloromethane) affords N-(4-decylphenyl)-2-hydroxy-[1,1'-biphenyl]-3-carboxamide (1.69 g, 90%), mp 74°-75° C.

Similarly, Examples 10-20 are prepared by the method of Example 9 and are found in Table 2.

TABLE 2

A compound of formula I wherein y is one, R$_5$ is hydrogen, b is one, and R$_1$ and R$_6$ are as shown:

R$_1$ Position

TABLE 2-continued

A compound of formula I wherein y is one, R₅ is hydrogen,
b is one, and R₁ and R₆ are as shown:

| Example | 3 | 4 | 5 | 6 | R₆ | Yield | mp (°C.) |
|---|---|---|---|---|---|---|---|
| 10 | H | H | Ph* | H | 4-(n-decyl) | 90% | 179–180 |
| 11 | H | Ph | H | H | 4-(n-decyl) | 35% | 155–157 |
| 12 | H | H | Br | H | 4-(n-decyl) | 74% | 172–174 |
| 13 | H | H | H | H | 4-(n-decyl) | 45% | 94–95 |
| 14 | H | H | Br | H | 4-[2-(3,4-dimethoxy-phenyl)ethyl] | 76% | 154–156 |
| 15 | H | Cl | H | H | 4-[2-(3,4-dimethoxy-phenyl)ethyl] | 80% | 166 |
| 16 | H | H | Cl | H | 4-(n-decyl) | 80% | 165 |
| 17 | H | H | CH₃ | H | 4-(n-decyl) | 73% | 127–128 |
| 18 | NO₂ | H | H | H | 4-(n-decyl) | 79% | 101–102 |
| 21 | H | H | NO₂ | H | 4-(n-decyl) | 87% | 137–138 |
| 22 | CH₃ | H | H | H | 4-(n-decyl) | 71% | 90–91 |
| 23 | Cl | H | H | H | 4-[2-(3,4-dimethoxyphenyl)ethyl] | 45% | 125 |
| 24 | Cl | Cl | H | H | 4-[2-(3,4-dimethoxyphenyl)ethyl] | 63% | 175–177 |
| 25 | H | H | H | OH | 4-(n-decyl) | 38% | 121–123 |
| 26 | H | Me | H | H | 4-[2-(3-methoxy-4-hydroxyphenyl)-ethyl] | 82% | 170 |
| 27 | Cl | Cl | H | H | 4-(n-decyl) | 81 | 154–155 |
| 28 | Cl | H | H | H | 4-(n-decyl) | 73 | 124 |
| 29 | H | CH₃ | H | H | 4-[2-(3-4-dibenzyloxyphenyl)ethyl]; N-methyl | 71 | non-crystalline |

| Example | R₁ | R₆ | % Yield | mp (°C.) |
|---|---|---|---|---|
| 30 | 3,4-(fused benzene ring) | 4-[2-(4-chloro phenyl)-ethyl] | 61 | 160–164 |
| 31 | 3,4-(fused benzene ring) | 4-2-(3,4-dichloro-phenyl)ethyl] | 37 | 166–168 |

EXAMPLE 32

Benzamide, N-(4-n-decylphenyl)-2-hydroxy-5-amino·hydrochloride

A methanol (75 ml) solution of N-(4-n-decylphenyl)-2-hydroxy-5-nitro-benzamide (890 mg, 2.23 mmol) and Raney-nickel (200 mg) is stirred at ambient temperature until the calculated pressure change is realized. The contents are filtered and acidified with concentrated HCl (0.2 ml). Removal of solvents affords 831 mg of the desired N-(4-n-decylphenyl)-2-hydroxy-5-aminobenzamide-hydrochloride, dc =240°–245° C.

EXAMPLE 33

3,5-Dichloro-N-(4-decylphenyl)-2-hydroxybenzamide

Under an argon atmosphere, a tetrahydrofuran (20 ml) solution of diisopropylamine (1.59 ml, 11.31 mmol) is cooled to 0° C. n-Butyllithium (2.3 M, 4.9 ml, 11.31 mmol) is added, after which the solution is allowed to stir an additional ten minutes. n-Decylaniline (2.64 g, 11.31 mmol) is then added and the solution allowed to stir for 15 minutes at ambient temperature. A tetrahydrofuran 925 ml) solution of methyl 3,5-dichlorosalicylate (1.00 g, 4.52 mmol) is added and the resulting solution is stirred for 45 minutes at ambient temperature. The contents are then poured into 10% hydrochloric acid (100 ml) and extracted into diethyl ether. The organics are washed with 10% hydrochloric acid, dried (sodium sulfate), and concentrated to give 3.47 g of a residue. Recrystallization from 2-propanol/water gives a 3,5-dichloro-N-(4-decylphenyl)-2-hydroxybenzamide (1.32 g, 69%), mp 90°–91° C.

Similarly prepared are Examples 34–42, which are found in Table 3.

TABLE 3

A compound of Formula I wherein y is one, R₅ is hydrogen, b is one, x is hydrogen and R₁ and R₆ are as shown:

| Example | R₁ Position 3 | 4 | 5 | R₆ | % Yield | mp (°C.) |
|---|---|---|---|---|---|---|
| 34 | Cl | H | H | 4-[2-(3,4-dichlorophenyl)ethyl] | 44% | 166–167 |
| 35 | H | NO₂ | H | 4-(n-decyl) | 40% | 180–181 |
| 36 | H | Cl | H | 4-[2-(3,4-dichlorophenyl)ethyl] | 34% | 203–204 |
| 37 | H | Cl | H | 4-[2-(3,4-dichlorophenyl)ethyl] | 57% | 214–215 |
| 38 | 4,5-(fused benzene ring) | | | 4-[2-(3,4-dimethoxyphenyl)ethyl] | 38 | 201–202 |
| 39 | 3,4-(fused benzene ring) | | | 4-[2-(3,4-dimethoxyphenyl)ethyl] | 48 | 179–180 |

TABLE 3-continued

A compound of Formula I wherein y is one, R₅ is hydrogen, b is one, x is hydrogen and R₁ and R₆ are as shown:

| Example | R₁ Position 3 | 4 | 5 | R₆ | % Yield | mp (°C.) |
|---|---|---|---|---|---|---|
| 40 | | 3,4 | | 4-[2-(1,1'-biphenyl-4-yl)ethyl]* | 39 | 196-198 |
| 41 | | | 5,6 | 4-[2-(3,4-dimethoxyphenyl)ethyl] | 74 | 148-150 |
| 42 | H | H | H | 4-[2-(3,4-dichlorophenyl)ethyl] | | 170 |

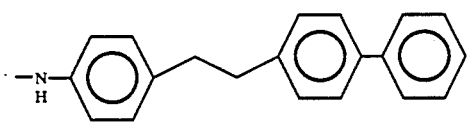

EXAMPLE 43

4-Methyl-N-methyl-N-[4-[2-(3,4-dihydroxyphenyl]ethyl]phenyl-2-hydroxybenzamide

To an ethyl acetate:methanol (1:1, 40 ml) solution of 4-methyl-N-methyl-N-[4-[2-(3,4-dibenzyloxyphenyl]ethyl]phenyl]-2-hydroxybenzamide (1.00 g, 1.80 mmol) is added 10% Pd/C (200 mg). The mixture is stirred under hydrogen atmosphere (1 atmosphere) for 12 hours. The catalyst is removed by filtration (Celite ®), and the filtrate then concentrated to give 740 mg of crude material. Flash chromatography (SiO₂: 95:5 CHCl₃:MeOH) affords 660 mg (97%) of 4-methyl-N-methyl-[4-(2-(3,4-dihydroxyphenyl)ethyl)phenyl]-2-hydroxybenzamide as a noncrystalline semisolid.

EXAMPLE 44

4-Chloro-N-[4-[2-(3,4-dihydroxyphenyl)ethyl]-2-hydroxybenzamide

A dichloromethane (40 ml) solution of 4-chloro-N-[4-[2-(3,4-dimethoxyphenyl)ethyl]phenyl]-2-hydroxybenzamide (0.50 g, 1.21 mmol) is cooled to −78° C. under an argon atmosphere. Boron tribromide (1.0M solution in dichloromethane, 5.5 ml, 5.5 mmol) is added, and the mixture is stirred at −78° C. for four hours, followed by stirring at ambient temperature for two hours. The solution is then recooled to −20° C. and quenched with water (5.5 ml). The mixture is allowed to stir at ambient temperature for 12 hours, after which additional water (10 ml) is added. Filtration affords 4-chloro-N-[4-[2-(3,4-dihydroxyphenyl)ethyl]phenyl]-2-hydroxybenzamide (0.42 g, 91%), mp 229°-213° C. after recrystallization from methanol/water.

EXAMPLE 45

N-[4-[2-(3,4-Dihydroxyphenyl)ethyl]phenyl]-2-hydroxy-4-methylbenzamide

A mixture of 2,2,7-trimethyl-4H-1,3,2-benzodioxasilin-4-one (2.0 g, 10 mmole) and 4-[2-[3,4-bis[(trimethylsilyl)oxy]phenyl]ethyl]benzenamine (3.0 g, 8 mmol) is heated under argon to 180° C. After three hours the mixture is cooled, triturated with pentane and filtered. The collected solid is rinsed several times with pentane and dried. Recrystallization from isopropanol gave the pure product (1.4 g), mp 201°-202° C.

EXAMPLE 46

N-[4-[2-(3,4-Dimethoxyphenyl)ethyl]phenyl]-2-hydroxy-4-methylbenzamide

The preparation is as described for Example 45 using 2,2,7trimethyl-4H-1,3,2-benzodioxasilin-4-one (2.0 g, 10 mmol) and 4-[2-(3,4-dimethoxyphenyl)ethyl]benzenamine (2.5 g, 10 mmol). Recrystallization from methanol/DMF gives the pure product (1.9 g) mp 162°-164° C.

EXAMPLE 47

Benzamide, N-[4-[2-(3,4-dihydroxyphenyl)ethyl]phenyl]-2-hydroxy

Prepared by the method described in Example 44 from benzamide, N-[4-[2-(3,4-dimethoxyphenyl)ethyl]phenyl]2-hydroxy. Recrystallization from water/2-propanol gives the product, mp 156°-158° C.

EXAMPLE 48

N-[4-[2-(3,4-dimethoxyphenyl)ethyl]phenyl]-2-hydroxybenzamide

A mixture of 2-acetoxybenzoylchloride (6.5 g, 0.033 mole) and 4-[2-(3,4-dimethoxyphenyl)ethyl]benzamine (6.5 g; 0.025 mmol) in xylene (300 ml) is stirred at room temperature and then heated to reflux for two hours when a clear solution is formed. The solvent is evaporated off under vacuum and the oil taken up in CH₂Cl₂, washed with sodium bicarbonate solution, with water and dried. The methylene chloride is distilled off. The residual oil is dissolved in hot isodipropyl ether to give the acetate derivative which is removed by filtration. The filtrate is evaporated off to give an oil. The crude oil is dissolved in methanol (150 ml) and 1(N) NaOH solvent (50 ml) and is heated to reflux for two hours. The reaction mixture is concentrated, diluted with cold water, and then acidified with 4N HCl (30 ml) when the product crystallized out. The crude product is recrystallized from methanol to give analytical sample (1.9 g), mp 149°-151°.

EXAMPLE 49

2-Naphthalenecarboxamide, N-(4-decylphenyl)-3-hydroxy

A suspension of 1.0 g (0.021 mole) of 50% sodium hydride/mineral oil in 25 ml of dimethyl sulfoxide under a nitrogen atmosphere is cooled in a cold water bath while 4.7 g (0.020 mole) of 4-(n-decyl)aniline is added. The mixture is stirred at room temperature for one hour, then treated in portions over 15 minutes with 2.0 g (0.0099 mole) of 3-hydroxy-2-naphthalene-carboxylic acid methyl ester. An additional 50 ml of dimethyl sulfoxide is added, and the mixture is stirred at room temperature for 45 hours. The reaction mixture is added to 500 g of ice/water and acidified with 4.0N hydrochloric acid. The gelatinous precipitate is filtered and distributed between the water (300 ml) and dichloromethane (100 ). The layers are separated and the aqueous layer is washed with fresh dichloromethane (2×150 ml). The combined organic layers are washed with water (1×250 ml), 1.0N hydrochloric acid (2×250 ml), and water again. The organic layer is dried (anhydrous sodium sulfate) and evaporated. Recrystallization of the residue from aqueous 2-propanol yield 1.4 g (35% yield) of the amide product. An additional recrystallization as above yields an analytically pure sample, mp 171°–173° C. V. Preparation of Compounds of Formula I Wherein y is 2

EXAMPLE 50

N-[4-[2-(3,4-dimethoxyphenyl)ethyl]phenyl]-2-hydroxy-5-chloro-α-oxo-benzeneacetamide Under an argon atmosphere, a tetrahydrofuran (20 ml) solution of 4-[2-(3,4-dimethoxyphenyl)ethyl]benzenamine (2.50 g, 9.72 mmol) is cooled to 0° C. n-Butyllithium (2.3M, 4.2 ml, 9.72 mmol) is added, and the resulting solution is stirred for 15 minutes. A tetrahydrofuran (10 ml) solution of ethyl 5-chloro-2-hydroxy-α-oxobenzenacetate (0.74 g, 3.24 mmol) is then added, after which the solution is allowed to warm to ambient temperature over a 30 minute period. The contents are then poured into 5% hydrochloric acid (100 ml) and extracted into ethyl acetate. The organics are washed with 10% sodium bicarbonate and brine, then dried (sodium sulfate), and concentrated to give 1.51 g of a crude solid. Chromatography (Kieselgel 60, dichloromethane) affords N-[4-[2-(3,4-dimethoxyphenyl)ethyl]phenyl]-2-hydroxy-5-chloro-α-oxobenzeneacetamide (0.86 g, 61%), mp 128°–130° C.

EXAMPLE 51

N-Methyl-N-[4-(2-(3,4-dimethoxyphenyl)ethyl)-phenyl]-2-hydroxy-α-oxo-benzeneacetamide Following the procedures of Example 50, N-methyl-N-[4-[2-(3,4-dimethoxyphenyl)ethyl]phenyl]-2-hydroxy-α-oxobenzenacetamide is prepared from N-methyl-N-4-[2-(3,4-dimethoxyphenyl)ethyl]benzenamine and ethyl-2-hydroxy-α-oxo-benzeneacetate in 22% yield.

EXAMPLE 52

N-[4-(2-(3,4-dimethoxyphenyl)ethyl)phenyl]-2-hydroxy-α-oxo-Benzeneacetamide

A mixture of 2,3-benzofurandione (Fries and Pfaffendorf, Ber, 45, 156 (1912); Valentine, Titoff, Muller, and Reichstein, *Helv. Chim. Acta,* 20, 883 (1937)) (10 g, 0.0675 mol) and 4-[2-(4-aminophenyl)ethyl]-1,2-dimethoxybenzene (15.6 g, 0.0606 mol) in dry tetrahydrofuran is stirred at room temperature under nitrogen for 18 hours in the dark. The solvent is removed under reduced pressure on a rotary evaporator below 35° and the resulting solid is recrystallized from tetrahydrofuran-ethanol to give 22.2 g (90.6%) of a light-yellow solid, mp 124°–125° C.

EXAMPLE 53

N-[4-[2-(3,4-dihydroxyphenyl)ethyl]-phenyl]-2-hydroxy-α-oxo-benzeneacetamide

A mixture of 2,3-benzofurandione (4.56 g, 0.0307 mole) and 1,2-benzenediol, 4-[2-(4-aminophenyl)ethyl](7.05 g, 0.0307 mole) in dry tetrahydrofuran is stirred at room temperature under nitrogen for 19 hours in the dark. The solvent is removed under reduced pressure on a rotary evaporator below 50° C. and the resulting solid is purified by column chromatography on silica-gel (260 g). Elution with ethyl acetate gave 10.7 g of a solid. Recrystallization fro acetonitrile with ice cooling gave 6.9 g (59.6%) of a light-yellow solid, mp 165°–167° C.

EXAMPLE 54

N-[4-[2-(3,4-dimethoxyphenyl)ethyl]phenyl]-3-(1,1-dimethylethyl)-2-hydroxy-α-oxo-benzeneacetamide A solution of 7-(1,1-dimethylethyl)-2,3-benzofurandione (1.0 g, 5 mmol) and 4-[2-(3,4-dimethoxyphenyl)ethyl]benzenamine (1.0 g, 4 mmol) in 10 ml of dichloromethane is stirred at room temperature for 48 hours. The solvent is evaporated and the residue crystallized from ether/hexane. Recrystallization from acetonitrile gave the pure product, (1.0 g) mp 143°–144° C.

EXAMPLE 55

N-[4-[2-(3,4-dihydroxyphenyl)ethyl]phenyl]-3-(1,1-dimethylethyl)-2-hydroxy-α-oxobenzenacetamide A mixture of 7-(1,1-dimethylethyl)-2,3-benzofurandione (3.7 g, 18 mmoles) and 4-2-(4-aminophenyl)ethyl]-1,2 -benzenediol (3.4 mmoles) in 30 ml of dichloromethane is stirred at room temperature for 24 hours. The solution is diluted with ether and filtered. The filtrate is evaporated under reduced pressure to leave the product as a syrup which eventually crystallizes. Recrystallization from ether/pet ether gave the the pure product (2.0 g) mp 138°–149° C.

The compounds in Tables 4 and 5 are prepared by the method described in Example 53.

TABLE 4

A compound of Formula I wherein y is two, b is one, and $R_1$ is hydrogen, and $R_5$ and $R_6$ are as shown.

| Example | $R_5$ | $R_6$ | mp °C. | Yield % | Recrystallization Solvent |
|---|---|---|---|---|---|
| 56 | 3-Cl | 4-Cl | 138–140 | 67 | Tetrahydrofuran/acetonitrile |
| 57 | H | 4-Cl | 145–146 | 69 | Tetrahydrofuran/acetonitrile |

TABLE 5

| Example | Compound | mp °C. | Description |
|---|---|---|---|
| 58 | 3-chloro-N-[4-[2-(3,4-dihydroxyphenyl)ethyl]-phenyl]-6-hydroxy-2,4-dimethyl-α-oxo-benzeneacetamide | 140–142 | Deep yellow solid |
| 59 | 3-chloro-N-[4-[2-(3,4-dimethoxyphenyl)ethyl]-phenyl]-6-hydroxy-2,4-dimethyl-α-oxo-benzeneacetamide | 163–164 | Fluffy off-white solid |
| 60 | 3-chloro-N-[4-[2-(3,4-dimethoxyphenyl)ethyl]-phenyl]-2-hydroxy-α-oxo-benzenacetamide | 125 | Yellow solid |

The preparation of 2,3-benzofurandione, 5-chloro-4,6-dimethyl is analogous to that described by R. Stolle and E. Knebel Ber. 59, 1216 (1921).

The usefulness of the compounds of the present invention as inhibitors of lipoxygenase enzyme or antagonists of leukotriene or other related biochemical actions is demonstrated by their effectiveness in various standard pharmacological test procedures. A description of each procedure follows.

Human Leukocyte Lipoxygenase Assay (LDA-H)

Whole blood is collected from normal volunteers and spun in a refrigerated centrifuge for four minutes at 1°–6° C. at 3800 g. The buffy coat is manually separated and washed twice with chilled 0.83% $NH_4Cl$ and centrifuged at 1000 RPM for ten minutes at 4° C. The white cell is suspended in culture media-EMEM supplemented with 6% Agamma human serum, tricine buffer, and neomycin and recentrifuged at 1000 g to yield a pellet containing the leukocytes used for the preparation of the acetone pentane powder.

The acetone-pentane powder is prepared utilizing a modification of the procedure reported for human platelet lipoxygenase. See Siegel, et al, Arachidonate Metabolism via Lipoxygenase and 12-L-hydroperoxy-5-Eicostetraenoic acid Peroxidase Sensitive to Antiinflammatory Drugs, *Proc. Natl. Acad. Sci.*, USA 77:308, 1980 and D. P. Wallach and V. R. Brown, a novel Preparation of Human Platlet Lipoxygenase, *Biochem. Biophys. Acta.* 663:361, 1981. Buffy coat prepared above is resuspended in 5-7 volumes of cold 0.1M Tris buffer, pH 7.4 containing 0.154M NaCl. The suspension is centrifuged at 13,300 g for ten minutes at 4° C. The resultant pellet was retained, resuspended in five volumes of cold acetone, recentrifuged at 13,300 g and resuspended in five volumes of cold pentane. The pentane suspension is centrifuged for ten minutes at 13,300 g to give a pellet which is dried in the cold under vacuum with periodic pulverization. The dry powder is stable for several weeks when stored at −88° C.

Enzyme stock solution is prepared in the following manner. About 15 mg of the acetone-pentane powder sis suspended in 4 ml of cold tris buffer (0.1M, pH 7.4), allowed to stand for five minutes, and homogenized thoroughly. The homogenate is sonicated three times for 15 seconds each time, diluted to 7 ml with cold tris buffer (0.1M, pH 7.4), and centrifuged at 4° C. for 60 minutes at 13,300 g. The supernatent is retained and diluted to a total of 10 ml with cold tris buffer (0.1M, pH 7.4) to give the stck enzyme solution. Additional dilutions of 2-50 fold are done as necessary to locate optimal enzyme reaction rate in the assay described below.

Substrate solution is prepared at 100 $\mu$M or 1.0 $\mu$M concentrations of arachidonic acid or linoleic acid in 0.1M tris buffer, pH 9.0 containing 20% ethanol.

The enzyme reaction is followed spectrophotometrically by the appearance of a conjugated diene product at 234 nm. The reaction is monitored at 24° C. using a Gilford Model 2600 spectrophotometer. Each assay had a total volume of 1.0 ml and contained substrate, tris buffer (0.1M, pH 9.0), 2% ethanol, and sufficient enzyme to give an easily measurable initial rate of reaction. The effects of inhibitors on the reaction are compared with control reactions run under indentical conditions. Routinely, each compounds of the present invention is incubated with the enzyme for five minutes prior to addition of substrate to initiate the reaction. Inhibition expressed as $IC_{50}$ as molar concentration of the compound required to reduce reaction rate to 50% control.

To Evaluate the Effect of Each Compounds as a 5-Lipoxygenase Inhibitor in Comparison to Standard Reference Agents in Human Leukocytes (5LOAI)

The purpose of this assay is to evaluate the activity of each compound as an inhibitor of human leukocyte 5-lipoxygenase.

Arachidonic acid and calcium ionophore A23187 are obtained from Sigma (St. Louis, MO). Silica gel plates, GF are obtained from Analtech (Newark, DE). Arachidonic acid, (1-$^{14}$C) and 5-HETE ($^3$H), 5-(S)-hydroxy-6-trans, 8,11,14-cis eicosatetraenoic acid, are obtained from New England Nuclear (Boston, MA). Six percent Dextran-70 in 0.9% NaCl is obtained from Cuffer Labs (Berkeley, CA).

Preparation of Leukocytes

Fresh blood from normal adult men who had not received any drugs for at least the previous five days is obtained by the Community Research Clinic (WL/PD) using venipuncture and collected into heparinized vacuotainer tubes. To every 100 ml of pooled blood is added 25 ml of dextran solution (6% dextran −70 in 0.9% sodium chloride containing 3% dextrose) and this is mixed gently in a plastic cylinder. The mixture is left to stand at room temperature for at least 90 minutes. The upper layer which is rich in leukocytes and platelets is then carefully decanted into 50 ml plastic tubes and centrifuged at about 100×g for eight minutes in and IEC centrifuge and rotor number 269 (about 600 rpm). The supernatant fluid is discarded and the pellet is resuspended in 10 ml of 0.87% ammonium chloride for exactly two minutes. This procedure is to lyse completely contaminating red blood cells. Leukocytes are then separated by centrifugation for ten minutes. The pellet is washed three times by suspension in 20 ml PBS (sodium chloride, 7.1 g; $Na_2HPO_4$, 1.15 g; $KH_2PO_4$,0.2 g, and KCl, 0.2 g/L) and centrifuged as before. The final pellet is suspended in PBS containing 0.87 mM $CaCl_2$. Viability of the cells is then checked using trypan blue exclusion method and is found to be over 90%.

5-Lipoxygenase Enzyme Assay

Leukocyte cells in suspension (0.98 ml) are incubated with or without test compounds for five minutes at 37° C. in a shaking water bath. At this time a 17 $\mu$l mixture is perpared per 1 ml of cell suspension: 100 mM arachidonic acid, 1 $\mu$l, 0.05 $\mu$Ci $^{14}$C-arachidonic acid in 5 $\mu$l; 1 mM calcium ionophore A23187, 10 $\mu$l (1). This mixture is added and the incubation continued for five minutes. The reaction is stopped by adding four volumes of absolute ethanol and the mixture is kept in ice for 30 minutes. The floculated precipitate is separated by centrifugation at about 37,000×g for 20 minutes (Beckman Instruments rotor number 40). The alcohol extract is taken to dryness under a stream of nitrogen and the residue is dissolved in 100–200 $\mu$l absolute ethanol. At the time any turbidity is removed by centrifugation. An aliquot (25–50 $\mu$l) is applied onto 20×20 cm silica gel TLC plate and developed using the following solvent system: diethyl ether, petroleum ether (2040°C.), acetic acid (50:50: 1 v/v). Zones of 1 cm apart are scraped from the TLC plate and transferred to mini-vials. Methanol (0.5 ml) is added to dissolve the radioactivity adsorbed to the silica gel and scintillation fluid (H. P., Beckman), 5 ml is then added and vials are counted in a liquid scintillation counter. A sample of $^3$H-5-HETE is applied and used for the identification of the formed 5-HETE. Total radioactivity in the test as well as the control samples are normalized and the amount of 5-HETE present is calculated accordingly.

$IC_{50}$ values are defined as the concentrations of test agents which caused a 50% inhibition of the formation of 5-HETE as compared to control and are determined by inspection of the concentration-response curves.

5-Lipoxygenase Assay Using Isolated Human Leukocytes (5LOA$_2$)

The formation of 5-HETE in human leukocytes is considered a measure of 5-lipoxygenase activity. The protocol is described in the following.

Fresh heparinized or EDTA treated human blood is mixed with 6% dextran-3% dextrose in isotonic saline in the ratio 0.25 ml dextran solution per 1.0 ml blood. After mixing the blood is allowed to sit at room temperature for about 90 minutes while the RBC's settle. During this period, the plasma is removed with a plastic pipette to nalgens tubes.

The plasma is centrifuged at 800 rpm (125 kg) on the Beckman Td-b refrigerated centrifuge to remove the platelets (which remain in the supernatant). The pellet, consisting of leukocytes and erythrocytes, is treated with 10 ml 0.87% ammonium chloride at room temperature for four minutes, lysing the red cells. At the end of four minutes the cells are diluted with a 2×volume of phosphate buffered saline, pH 7.4, and centrifuged for ten minutes. The cells are washed three times with the phosphate buffered saline. Any of the pelleted cell matter which is not easily resuspended is discarded during the washings —the material contains platelets (12-lipoxygenase activity).

After washing, the cells are resuspended in phosphate buffered saline containing 1.0 mM calcium and 0.5 mM magnesium. After counting the cells are diluted to 1.5–2.0×10$^7$ leukocytes per milliliter.

To each polypropylene reaction tube is added 0.48 ml leukocytes in Ca-Mg phosphate buffered saline, pH 7.4; 1–5 μl test compound dissolved in DMSO and buffer; or DMSO for control tubes.

The tubes preincubate at 37° C. for five minutes.

The reaction is started by adding 20 μl of the following, 0.5 μl 20 mM arachidonic acid —final concentration =20 μm; 1 μl 5 mM calcium ionophore A23187 -final concentration =10 μm; and 18.5 μl buffer.

The reactioin proceeds for five minutes, then is stopped by adding 0.5 ml 0.5 mM ice cold Tris buffer, pH 8.0. The tubes are chilled on ice for ten minutes and then extracted three times with a total of 3.5 ml ethyl acetate (3.0 ml removed).

The tubes can be stored at this point. For extended storage, the tubes should be filled with nitrogen.

The ethyl acetate is evaporated with a Sorvall Speed-Vac. The residue is dissolved in ethanol. The tubes can also be stored at this point at −20° C. under nitrogen.

A portion of the ethanol solution is injected into the HPLC system for 5-HETE quantitation.

The HPLC system consists of Hewlett-Packard 1040A UV spectrophotometry system with an HP85 computer. Injections are made automatically with a Waters WISP 710B. The pump is a Spectra Physics SP8700. Peaks are measured with a Hewlett Packard 3360A integrator. An RP C-18 column is used. The solvent system is isocratic; the solvent is 70% methanol and 30% 0.01M sodium acetate, pH 5.7, pumped at 1.0 ml/min. The flow is monitored at 235 nm for 5-HETE quatitation. Using a 15 cm Alltech Nucleosil C-18 5 μM column provides for a sample turnaround time of about 16 minutes.

Ic$_{50}$ is calculated as the amount of test agent that causes 50% inhibition of the formation of 5-HETE relative to the control.

When tested by the above described procedures and shown by the notations of the acronym for each test, various compounds of the Formula I as defined above indicated activity at the highest dose tested as shown in Table 6.

TABLE 6

| | Concentration (M) | % Inhibition | |
|---|---|---|---|
| Example 49 | | | |
| 5LOA | 5.00 E* −6 | 11.6 | |
| | 2.00 E −5 | 17.9 | |
| LDAH | 2.50 E −5 | 0.0 | |
| Example 52 | | | |
| 5LOA | 5.00 E −6 | 50.0 | IC50 |
| LDAH | 1.84 E −7 | 50.0 | IC50 |
| Example 53 | | | |
| 5LOA | 3.38 E −6 | 50.0 | IC50 |
| LDAH | 1.70 E −5 | 50.0 | IC50 |
| Example 48 | | | |
| 5LOA | 4.20 E −6 | 50.0 | IC50 |
| | 3.50 E −6 | 50.0 | IC50 |
| LDAH | 2.50 E −5 | 0.0 | |
| Example 47 | | | |
| LDAH | 2.50 E −5 | 0.0 | |
| Example 46 | | | |
| 5LOA | 5.00 E −7 | 50.0 | IC50 |
| 5LOA2 | 1.69 E −6 | 50.00 | |
| LDAH | 1.40 E −5 | 50.00 | IC50 |
| Example 54 | | | |
| 5LOA | 1.00 E −5 | 6.5 | |
| | 2.00 E −5 | 6.0 | |
| | 4.00 E −5 | 14.5 | |
| LDAH | 2.80 E −7 | 50.0 | IC50 |
| Example 55 | | | |
| 5LOA | 7.10 E −6 | 50.0 | IC50 |
| | 8.17 E −6 | 50.0 | IC50 |
| LDAH | 3.90 E −6 | 50.0 | IC50 |
| Example 2 | | | |
| 5LOA | 1.00 E −5 | 11.3 | |
| | 4.00 E −5 | 13.3 | |
| Example 8 | | | |
| 5LOA | 7.10 E −6 | 50.0 | IC50 |
| Example 7 | | | |
| 5LOA | 4.00 E −5 | 18.9 | |
| | 1.00 E −5 | 16.4 | |
| LDAH | 2.80 E −6 | 50.0 | IC50 |
| Example 12 | | | |
| LDAH | 2.50 E −5 | 0.0 | |
| Example 13 | | | |
| 5LOA | 1.00 E −4 | +1.3 | |
| | 1.00 E −4 | +12.2 | |
| LDAH | 2.50 E −5 | 0.0 | |
| Example 36 | | | |
| LDAH | 2.50 E −5 | 0.0 | |
| Example 37 | | | |
| LDAH | 5.45 E −7 | 50.0 | IC50 |
| Example 34 | | | |
| 5LOA | 3.92 E −5 | 50.0 | IC50 |
| Example 38 | | | |
| LDAH | 2.50 E −5 | 0.0 | |
| Example 9 | | | |
| 5LOA | 5.00 E −6 | 6.5 | |
| | 1.00 E −5 | 20.9 | |
| | 2.00 E −5 | 21.3 | |
| | 1.00 E −4 | +9.6 | |
| | 1 00 E −4 | +3.3 | |
| Example 45 | | | |
| 5LOA | 5.00 E −6 | 32.9 | |
| | 2.00 E −5 | 46.0 | |
| Example 56 | | | |
| 5LOA | 5.00 E −6 | 5.0 | |
| | 2.00 E −5 | 13.3 | |
| | 5.00 E −6 | +18.4 | |
| | 1.50 E −5 | +20.3 | |
| | 2.50 E −5 | +2.5 | |
| Example 57 | | | |
| 5LOA | 5.00 E −6 | 4.6 | |
| | 1.00 E −5 | 7.2 | |
| | 2.00 E −5 | 5.0 | |

TABLE 6-continued

| | Concentration (M) | % Inhibition |
|---|---|---|
| Example 35 | | |
| 5LOA | 5.00 E −6 | 1.7 |
| | 2.00 E −5 | 6.0 |
| Example 21 | | |
| 5LOA | 2.08 E −5 | 50.0 IC50 |
| Example 22 | | |
| LDAH | 6.80 E −7 | 50.0 IC50 |
| Example 60 | | |
| LDAH | 1.20 E −4 | 50.0 IC50 |
| Example 23 | | |
| LDAH | 4.10 E −6 | 50.0 IC50 |
| Example 25 | | |
| LDAH | 8.00 E −5 | 0.0 |
| Example 26 | | |
| 5LOA | 5.00 E −6 | 0.6 |
| | 2.00 E −5 | 7.6 |
| LDAH | 2.40 E −5 | 50.0 IC50 |
| Example 32 | | |
| 5LOA | 1.00 E −4 | 16.4 |
| | 1.00 E −4 | 11.5 |
| Example 43 | | |
| 5LOA | 5.30 E −6 | 50.0 IC50 |
| Example 51 | | |
| 5LOA | 1.11 E −5 | 50.0 IC50 |
| Example 42 | | |
| 5LOA2 | 5.00 E −6 | 21.1 |
| | 2.00 E −5 | 30.9 |

*The notation E −number means "X $10^{-no}$".

Accordingly, the present invention also includes a pharmaceutical composition for treating one of the above diseases of conditions comprising an antidisease or anticondition effective amount of a compound of the Formula I as defined above together with a pharmaceutically acceptable carrier.

The present invention further includes a method for treating one of the above named diseases or conditions in mammals, including man, suffering therefrom comprising administering to such mammals either orally or parenterally a corresponding pharmaceutical composition containing a compound of Formula I as defined above in appropriate unit dosage form.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders or tablet disintegrating agents; it can also be encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby to solidify.

Liquid form preparations include solutions, suspensions, and emulsions. As an example may be mentioned water or water propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing the liquid form preparation may be water, isotonic water, ethanol, glycerine, propylene glycol and the like as well as mixtures thereof. Naturally, the liquid utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these in packaged form.

The quantity of active compound in a unit dose of preparation may be varied or adjusted from 10 mg to 2 g preferably to 10 to 500 mg according to the particular application and the potency of the active ingredient. The compositions can, if desired, also contain other compatible therapeutic agents.

In therapeutic use as described above, the dosages may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter the dosage is increased by small increments until the optimum effect under the circumstances is reached. For convenience, the total daily dosage may be divided and administered in portions during the day if desired.

FORMULA

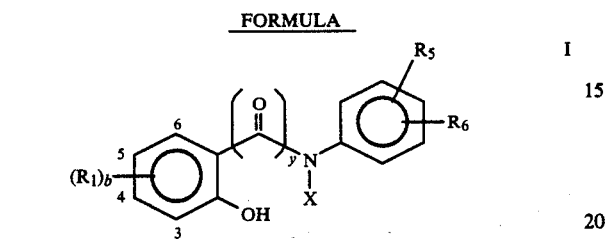

SCHEME I (A)

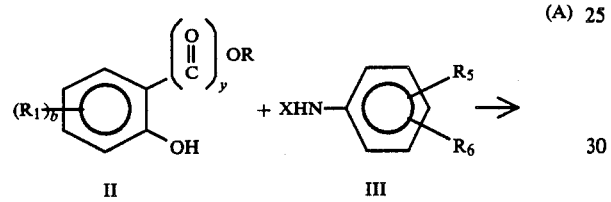

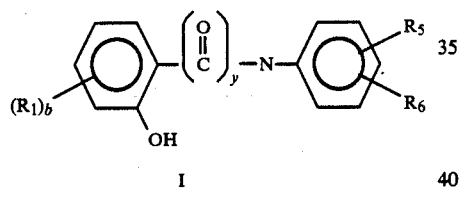

or (B)

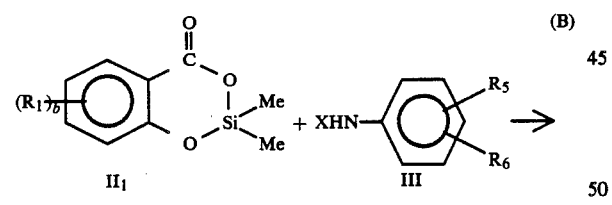

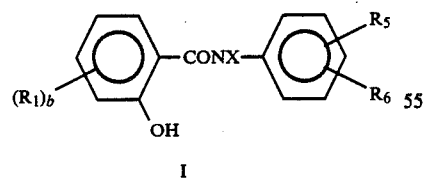

wherein y = 1

(C)

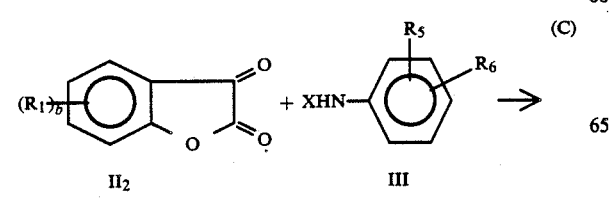

-continued
SCHEME I

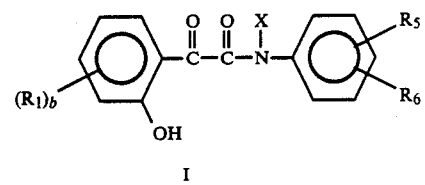

wherein y = 2

SCHEME II

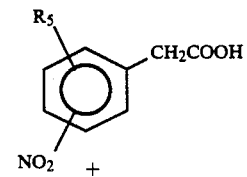

+

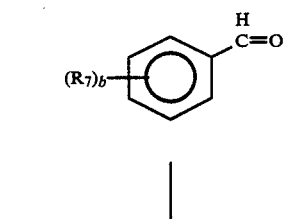

↓

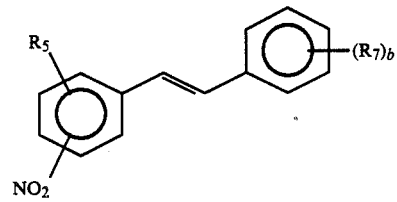   IV$_1$

SCHEME III

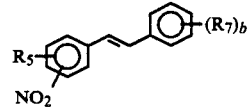   IV$_1$

H$_2$ Raney Nickel     Fe and HCl or dithionite

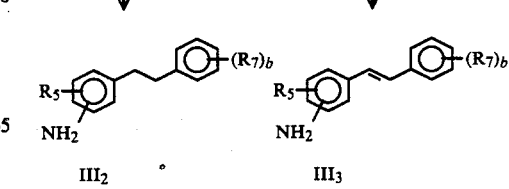

SCHEME IV

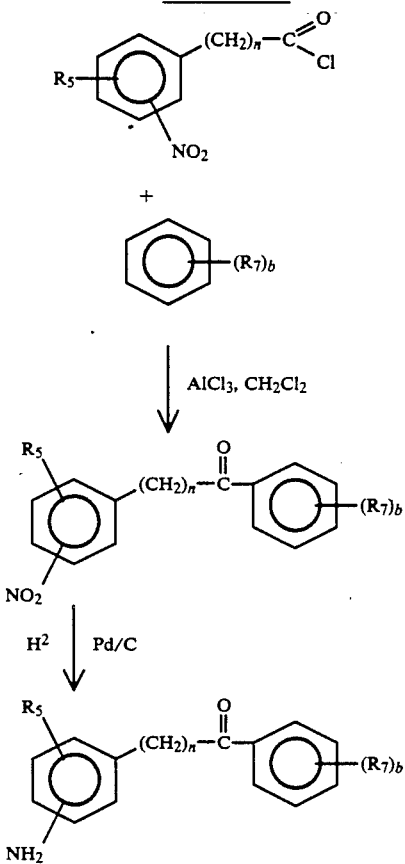

SCHEME V

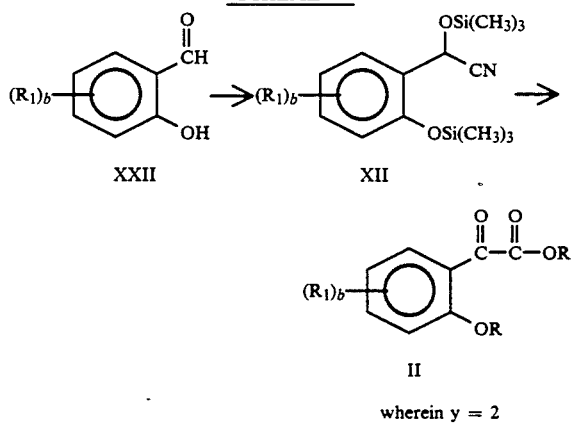

wherein y = 2

What is claimed is:
1. A compound having the formula

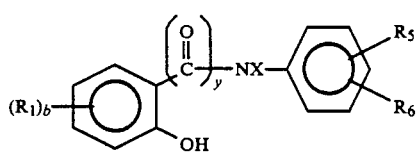

and pharmaceutically acceptable salts thereof, where (1) y is two: (2) b is zero, one, two, three, or four; (3) $R_1$ is selected from a group consisting of alkyl of from one to four carbons, inclusive; alkoxy of from one to four carbons, inclusive; thioalkoxy of from one to four carbon atoms, inclusive; carboalkoxy of from two to four carbons, inclusive; alkanoyl of from one to four carbons; hydroxy; halogen; nitro; amino; mono- and dialkylamino having each alkyl the same or different and when taken together are of from one to four carbons, inclusive; carbalkoxyamino of from one to four carbons, inclusive; alkylsulfinyl of from one to four carbons, inclusive; alkylsulfonyl of from one to four carbons, inclusive; and when b is one, then $R_1$ is —(CH=CH—CH=CH)— taken together with an adjacent ring carbon to form a benzo radical; (4) $R_5$ is hydrogen; alkyl of from one to four carbons, inclusive; alkoxy of from one to four carbons, inclusive; carboalkoxy of from two to four carbons, inclusive; hydroxy; halogen; or —(CH=CH—CH=CH)— taken together with adjacent carbons to form a benzo radical; (5) $R_6$ is alkyl of from six to twenty carbons, —CH=CH—$R_4$, —(CH$_2$)$_n$COR$_4$, or —(CH$_2$)$_n$—$R_4$ wherein n is zero to four, inclusive; and $R_4$ is phenyl optionally substituted at the two through six positions by lower alkoxy carbonyl; alkyl of from one to four carbons; alkoxy, or thioalkoxy of from one to four carbons, inclusive; phenalkoxy of from one to four carbons, inclusive; amino, monoalkyl and dialkyl amino having the alkyl of from one to four carbons, inclusive; alkanoylamino of from one to four carbons, inclusive; carboxyl; benzo; halogen; hydroxy; hydroxyalkyl of from one to four carbons, inclusive; alkanoyl of from one to four carbons, inclusive; nitro, alkanesulfonamido of from one to four carbons, inclusive; (6) X is hydrogen or lower alkyl of from one to four carbons.

2. A compound according to claim 1, and being N-[4-[2-(3,4-dimethoxyphenyl)ethyl]phenyl]-2-hydroxy-5-chloro-α-oxo-benzeneacetamide.

3. A compound according to claim 1, and being N-[4-[2-(3,4-dimethoxyphenyl)ethyl]phenyl]-2-hydroxy-α-oxo-benzeneacetamide.

4. A compound according to claim 1, and being N-[4-[2-(3,4-dihydroxyphenyl)ethyl]phenyl]-2-hydroxy-α-oxo-benzeneacetamide.

5. A compound according to claim 1, and being N-[4-[2-(3,4-dimethoxyphenyl)ethyl]phenyl]-3-(1,1-dimethylethyl)-2-hydroxy-α-oxo-benzeneacetamide.

6. A compound according to claim 1, and being N-[4-[2-(3,4-dihydroxyphenyl)ethyl]phenyl]-3-(1,1-dimethylethyl)-2-hydroxy-α-oxobenzeneacetamide.

7. A compound according to claim 1, and being 3-chloro-N-[4-[2-(3,4-dihydroxyphenyl)ethyl]phenyl]-6-hydroxy-2,4-dimethyl-α-oxo-benzeneacetamide.

8. A compound according to claim 1, and being 3-chloro-N-[4-[2-(3,4-dimethoxyphenyl)ethyl]phenyl]-6-hydroxy-2,4-dimethyl-α-oxo-benzeneacetamide.

9. A compound according to claim 1, and being 3-chloro-N-[4-[2-(3,4-dimethoxyphenyl)ethyl]phenyl]-2-hydroxy-α-oxo-benzeneacetamide.

10. A compound according to claim 1, and being N-[4-[2-(3,4-dimethoxyphenyl)ethyl]phenyl]-2-hydroxy-N-methyl-α-oxo-benzeneacetamide.

11. A compound according to claim 1, and being N-4-[2-(3,4-dichlorophenyl)ethyl]phenyl]-2-hydroxy-α-oxo-benzamide.

12. A pharmaceutical composition comprising a therapeutically effective amount of a compound as claimed in claim 1 together with a pharmaceutically acceptable carrier.

* * * * *